United States Patent
Smith et al.

(10) Patent No.: US 9,688,603 B2
(45) Date of Patent: *Jun. 27, 2017

(54) POLYHYDROXYALKANOATE DERIVATIVES, PREPARATION AND USES THEREOF

(71) Applicant: MICROMIDAS, INC., West Sacramento, CA (US)

(72) Inventors: Ryan L. Smith, Sacramento, CA (US); John Bissell, Sacramento, CA (US); Makoto N. Masuno, Elk Grove, CA (US); Douglas Cannon, Sacramento, CA (US); Alex B. Wood, Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/154,804

(22) Filed: May 13, 2016

(65) Prior Publication Data

US 2017/0096385 A1    Apr. 6, 2017

Related U.S. Application Data

(63) Continuation of application No. 14/404,384, filed as application No. PCT/US2013/043716 on May 31, 2013, now Pat. No. 9,359,283.

(60) Provisional application No. 61/653,750, filed on May 31, 2012, provisional application No. 61/785,825, filed on Mar. 14, 2013.

(51) Int. Cl.
*C07C 69/66* (2006.01)
*C07C 67/31* (2006.01)
*C07C 67/30* (2006.01)

(52) U.S. Cl.
CPC .............. *C07C 67/31* (2013.01); *C07C 67/30* (2013.01)

(58) Field of Classification Search
CPC ......... C07C 67/03; C07C 1/24; C07C 29/149; C07C 51/16; C07C 11/167; C07C 31/207; C07C 57/15; C07C 69/533; C07C 69/675; C07C 2527/167; C07C 29/095; C07C 67/31; C07C 69/56
See application file for complete search history.

(56) References Cited

U.S. PATENT DOCUMENTS

| | | | |
|---|---|---|---|
| 5,107,016 A | 4/1992 | Pennetreau | |
| 5,264,617 A | 11/1993 | Brake | |
| 6,472,188 B1 | 10/2002 | Lee et al. | |
| 6,534,599 B2 | 3/2003 | Marchessault et al. | |
| 6,780,911 B2 | 8/2004 | Zhong et al. | |
| 6,844,447 B2 | 1/2005 | Zhong et al. | |
| 6,933,404 B2 | 8/2005 | Zhong et al. | |
| 7,094,840 B2 | 8/2006 | Whitehouse et al. | |
| 7,230,144 B2 | 6/2007 | Zhong et al. | |
| 8,093,022 B2 | 1/2012 | Skraly et al. | |
| 8,114,643 B2 | 2/2012 | Skraly et al. | |
| 8,263,373 B2 | 9/2012 | Herrema et al. | |
| 8,283,435 B2 | 10/2012 | Whitehouse | |
| 8,524,856 B2 | 9/2013 | Krishnaswamy et al. | |
| 9,359,283 B2 | 6/2016 | Smith et al. | |
| 2002/0042481 A1 | 4/2002 | Marchessault et al. | |
| 2002/0043737 A1 | 4/2002 | Zhong et al. | |
| 2002/0077269 A1 | 6/2002 | Whitehouse et al. | |
| 2003/0144551 A1 | 7/2003 | Zhong et al. | |
| 2003/0158274 A1 | 8/2003 | Zhong et al. | |
| 2003/0158441 A1 | 8/2003 | Zhong et al. | |
| 2003/0162851 A1 | 8/2003 | Zhong et al. | |
| 2005/0222458 A1 | 10/2005 | Craciun et al. | |
| 2006/0084161 A1 | 4/2006 | Yanagita et al. | |
| 2006/0088921 A1 | 4/2006 | Yu | |
| 2006/0105440 A1 | 5/2006 | Kinoshita et al. | |
| 2006/0247390 A1 | 11/2006 | Whitehouse et al. | |
| 2010/0055628 A1 | 3/2010 | McMurry et al. | |
| 2010/0216902 A1 | 8/2010 | Wendelin et al. | |
| 2011/0046339 A1 | 2/2011 | Park et al. | |
| 2011/0223365 A1 | 9/2011 | Selionov et al. | |
| 2011/0275729 A1 | 11/2011 | Scandola et al. | |
| 2011/0293865 A1 | 12/2011 | Padwa et al. | |
| 2012/0021471 A1 | 1/2012 | Martin et al. | |
| 2012/0060413 A1 | 3/2012 | Somleva et al. | |
| 2012/0077238 A1 | 3/2012 | Herrema et al. | |
| 2012/0129232 A1 | 5/2012 | Skraly et al. | |
| 2012/0165500 A1 | 6/2012 | Herrema et al. | |
| 2012/0180162 A1 | 7/2012 | Patterson et al. | |

(Continued)

FOREIGN PATENT DOCUMENTS

| | | |
|---|---|---|
| EP | 0377260 A1 | 7/1990 |
| EP | 0628533 A1 | 12/1994 |

(Continued)

OTHER PUBLICATIONS

International Preliminary Report on Patentability received for PCT Patent Application No. PCT/US2013/043716, mailed on Dec. 11, 2014, 11 pages.

(Continued)

*Primary Examiner* — Yevegeny Valenrod
*Assistant Examiner* — Blaine G Doletski
(74) *Attorney, Agent, or Firm* — Morrison & Foerster LLP

(57) ABSTRACT

Provided herein are methods that utilize polyhydroxyalkanoates (PHAs) as a substrate for further conversion to C4 and C5 compounds. Polyhydroxyalkanoates can undergo esterification to yield alkyl hydroxyalkanoates and alkyl alkenoates, which may serve as useful precursors in the production of alkadienes and alkenedioic acids, including for example butadiene and butenedioic acid.

12 Claims, 3 Drawing Sheets

(56) References Cited

U.S. PATENT DOCUMENTS

| | | | |
|---|---|---|---|
| 2012/0328523 A1 | 12/2012 | Williams et al. |
| 2013/0005006 A1 | 1/2013 | Herrema et al. |
| 2013/0090449 A1 | 4/2013 | Whitehouse |
| 2013/0225761 A1 | 8/2013 | Whitehouse |
| 2013/0288317 A1 | 10/2013 | Ramseier et al. |

FOREIGN PATENT DOCUMENTS

| | | | |
|---|---|---|---|
| EP | 1036190 | B1 | 5/2005 |
| EP | 1609868 | A1 | 12/2005 |
| EP | 1330503 | B1 | 5/2011 |
| EP | 2431475 | A2 | 3/2012 |
| EP | 1964879 | B1 | 6/2012 |
| EP | 1654373 | B1 | 8/2012 |
| EP | 2196484 | B1 | 8/2012 |
| EP | 1529072 | B1 | 9/2012 |
| EP | 2291429 | B1 | 6/2013 |
| WO | 99/29889 | A1 | 6/1999 |
| WO | 02/34857 | A2 | 5/2002 |
| WO | 03/051813 | A1 | 6/2003 |
| WO | 03/062439 | A1 | 7/2003 |
| WO | 2008/058303 | A1 | 5/2008 |
| WO | 2008/062996 | A1 | 5/2008 |
| WO | 2010/008447 | A1 | 1/2010 |
| WO | 2010/036884 | A1 | 4/2010 |
| WO | 2010/044112 | A1 | 4/2010 |
| WO | 2010/075330 | A1 | 7/2010 |
| WO | 2010/151558 | A1 | 12/2010 |
| WO | 2011/100601 | A1 | 8/2011 |
| WO | 2011/100608 | A1 | 8/2011 |
| WO | 2012/037324 | A2 | 3/2012 |
| WO | 2012/122343 | A2 | 9/2012 |
| WO | 2012/142100 | A1 | 10/2012 |
| WO | 2012/149162 | A2 | 11/2012 |
| WO | 2012/149407 | A1 | 11/2012 |
| WO | 2013/142033 | A1 | 9/2013 |

OTHER PUBLICATIONS

International Search Report and Written Opinion received for PCT Patent Application No. PCT/US2013/043716, mailed on Sep. 2, 2013, 14 pages.
Non Final Office Action received for U.S. Appl. No. 14/404,384, mailed on Jun. 29, 2015, 6 pages.
Notice of Allowance received for U.S. Appl. No. 14/404,384, mailed on Feb. 9, 2016, 8 pages.
Anderson, et al., "Occurrence, Metabolism, Metabolic Role, and Industrial Uses of Bacterial Polyhydroxyalkanoates", Microbiological Reviews, vol. 54, No. 4, Dec. 1990, pp. 450-472.
Ariffin, et al., "Non-random Degradation Behavior of Poly(3-hydroxybutyrate) In Pyrolysis", Polymer Preprints, vol. 49, No. 2, 2008, pp. 451-452.
Eisenfuhr, et al., "A Ribozyme with Michaelase Activity: Synthesis of the Substrate Precursors", Bioorganic & Medicinal Chemistry, vol. 11, 2003, pp. 235-249.
Genta, et al., "Development of Chemical Recycling Process for Post-Consumer PET Bottles by Methanolysis in Supercritical Methanol", Mitsubishi Heavy Industries, vol. 40, Jan. 2003, 6 pages.
Ghate, et al., "PHB Production Using Novel Agro-industrial Sources from Different Bacillus Species", International Journal of Pharma and Bio Sciences, vol. 2, Issue 3, Jul.-Sep. 2011, pp. B-242-249.
Karr, et al., "Analysis of Poly-$\beta$-Hydroxybutyrate in Rhizobium japonicum Bacteroids by Ion-Exclusion High-Pressure Liquid Chromatography and UV Detection", Applied and Environmental Microbiology, vol. 46, No. 6, Dec. 1983, pp. 1339-1344.
Kuriyama, et al., "A Homogeneous Catalyst for Reduction of Optically Active Esters to the Corresponding Chiral Alcohols without Loss of Optical Purities", Advanced Synthesis & Catalysis, vol. 352, 2010, pp. 92-96.
Nakatsuka, et al., "Total Synthesis of Bicyclomycin", Tetrahedron Letters, vol. 24, No. 50, 1983, pp. 5627-5630.
Otera, Junzo, "Transesterification", Chemical Reviews, American Chemical Society, vol. 93, No. 4, 1993, pp. 1449-1470.
Saeed, et al., "Characterization of Partially Transesterified Poly($\beta$-hydroxyalkanoate) Using Matrix-assisted Laser Desorption/Ionization Time-of-flight Mass Spectrometry", Rapid Communications in Mass Spectrometry, vol. 13 1999, pp. 1951-1957.
Seebach, et al., "Uber die Depolymerisierung von Poly-(R)-3-Hydroxy-Buttersaeureester (PHB)", Helvetica Chimica Acta, vol. 65, No. 2, 1982, pp. 495-503.
Tsuge, et al., "Biosynthesis of Polyhydroxyalkanoate (PHA) Copolymer from Fructose Using Wild-Type and Laboratory-Evolved PHA Synthases", Macromolecular Bioscience, vol. 5, 2005, pp. 112-117.
Ugur, et al., "Accumulation of Poly-$\beta$-Hydroxybutyrate in Streptomyces Species During Growth with Different Nitrogen Sources", Turkish Journal of Biology, vol. 26, Jan. 24, 2002, pp. 171-174.
Vadola, "Riley Oxidation", Synthesis Literacy Group, Aug. 15, 2008, 14 pages.
Waldmann, Petru ,"Uber die Dehydratisierung von Alkoholen mittels Phthalsaureanhydrids (I. Mitteil.)", Chemische Berichte, vol. 83, No. 3, 1950, pp. 287-291.

POLYHYDROXYALKANOATE DERIVATIVES, PREPARATION AND USES THEREOF

CROSS REFERENCE TO RELATED APPLICATIONS

This application is a continuation application of U.S. patent application Ser. No. 14/404,384, which is a U.S. National Phase patent application of PCT/US2013/043716, filed internationally on May 31, 2013, which claims the benefit of U.S. Provisional Patent Application Ser. No. 61/653,750 filed May 31, 2012, and U.S. Provisional Patent Application Ser. No. 61/785,825 filed Mar. 14, 2013, the disclosures of which are hereby incorporated herein by reference in their entirety.

FIELD

The present disclosure relates generally to the preparation of polyhydroxyalkanoate (PHA) derivatives, and more specifically to the preparation of alkyl hydroxyalkanoates, alkyl alkenoates, alkanediols, alkadienes, and alkenedioic acids from PHAs.

BACKGROUND

Commodity chemicals useful for making plastics, rubbers, coatings, additives and fuels are often produced from petroleum-based sources. For example, butadiene is used in the manufacture of synthetic rubber; however, butadiene is commercially produced as a by-product of ethylene production from steam cracking, in which the crude C4 stream is fed to extraction units where butadiene is separated from other C4s by extractive distillation. Butenedioic acid is another example of a chemical, useful in the manufacture of various polyester resins, surface coatings, lubricant additives, plasticizers, copolymers and agricultural chemicals; however, butenedioic acid is typically derived from the hydrolysis of maleic anhydride, which is produced by oxidation of benzene or butane.

Due to increasing petroleum costs and high greenhouse gas emissions from the petroleum-derived carbon content, however, recent efforts have focused on developing bio-based chemicals that are at least partially derived from renewable sources. Thus, there is an ongoing need in the art for processes to produce chemicals, such as butadiene and butenedioic acid, as well as their intermediates, from non-petroleum sources on a commercially-viable scale.

BRIEF SUMMARY

The present disclosure addresses this need by providing methods to produce various derivatives of polyhydroxyalkanoates (PHAs), which are a class of polyesters that can be derived from renewable sources, such as biomass. Provided herein are methods that utilize PHAs as a substrate for further conversion to four-carbon (C4) and five-carbon (C5) compounds. For example, PHAs can undergo trans-esterification to yield alkyl hydroxyalkanoates and alkyl alkenoates, which may serve as useful precursors in the production of alkadienes and alkenedioic acids, including for example butadiene and butenedioic acid.

In one aspect, provided is a method for producing alkyl hydroxyalkanoate, alkyl alkenoate, or a mixture thereof, by: a) providing a PHA; b) providing an alcohol; and c) contacting the PHA with the alcohol to convert at least a portion of the PHA to alkyl hydroxyalkanoate, alkyl alkenoate, or a mixture thereof.

In some embodiments, the PHA is contacted with the alcohol at a temperature between 150° C. and 350° C., between 1.80° C. and 320° C., between 220° C. and 300° C., or between 240° C. and 260° C.; and/or at a pressure between 500 psi and 3000 psi, between 800 psi and 3000 psi, between 1000 psi and 2000 psi, between 1000 psi and 1600 psi, or between 1200 psi and 1500 psi. In one embodiment, the PHA is contacted with the alcohol at a temperature between 150° C. and 350° C. and/or at a pressure between 1000 psi and 3000 psi, before contact with the PHA. In another embodiment, the PHA is contacted with the alcohol at a temperature is between 200° C. and 300° C. and/or at a pressure between 600 psi 3000 psi.

In certain embodiments, the alcohol is provided in step (b), before contact with the PHA, at a temperature between 150° C. and 350° C., between 180° C. and 320° C., between 220° C. and 300° C., or between 240° C. and 260° C.; and/or at a pressure between 500 psi and 3000 psi, between 800 psi and 3000 psi, between 1000 psi and 2000 psi, between 1000 psi and 1600 psi, or between 1200 psi and 1500 psi. In one embodiment, the alcohol is provided in step (b), before contact with the PHA, at a temperature between 150° C. and 350° C. and/or at a pressure between 1000 psi and 3000 psi. In another embodiment, the alcohol is provided in step (b), before contact with the PHA, at a temperature is between 200° C. and 300° C., and/or at a pressure between 600 psi 3000 psi.

In certain embodiments, the alcohol provided in step (b), before contact with the PHA, is a critical alcohol, a supercritical alcohol or a near-critical alcohol.

In other embodiments, step (c) further includes heating the PHA and the alcohol to a temperature between 150° C. and 350° C., between 180° C. and 320° C. between 220° C. and 300° C. or between 240° C. and 260° C.; and/or at a pressure between 500 psi and 3000 psi, between 800 psi and 3000 psi, between 1000 psi and 2000 psi, between 1000 psi and 1600 psi, or between 1200 psi and 1500 psi. In one embodiment, step (c) further includes heating the PHA and the alcohol to a temperature between 150° C. and 350° C., and/or at a pressure between 1000 psi and 3000 psi. In another embodiment, step (c) further includes heating the PHA and the alcohol to a temperature is between 200° C. and 300° C., and/or at a pressure between 600 psi 3000 psi.

In other embodiments, step (c) further includes heating the PHA and the alcohol to critical, supercritical or near-critical conditions to produce alkyl hydroxyalkanonte, alkyl alkenoate, or a mixture thereof.

In some embodiments, the PHA is contacted with the alcohol at a temperature and a pressure sufficient to produce the alkyl hydroxyalkanoate in excess of the alkyl alkenoate. In other embodiments, the PHA is contacted with the alcohol at a temperature and a pressure sufficient to produce the alkyl alkenoate in excess of the alkyl hydroxyalkanoate.

In other embodiments, the PHA is contacted with the alcohol for a residence time sufficient to produce the alkyl hydroxyalkanoate in excess of the alkyl alkenoate. In yet other embodiments, the PHA is contacted with the alcohol for a residence time sufficient to produce the alkyl alkenoate in excess of the alkyl hydroxyalkanoate. In some embodiments, the PHA is contacted with the alcohol for a residence time of less than 48 hours, 24 hours, 16 hours, 12 hours, 6 hours, 4 hours, 2 hours, 1 hour, 30 minutes, 20 minutes, 15 minutes, 10 minutes, 5 minutes, 1 minute, or 30 seconds.

In some embodiments, the method further includes contacting the PHA and the alcohol with a solvent to convert at least a portion of the PHA to alkyl hydroxyalkanoate, alkyl alkenoate, or a mixture thereof. In various embodiments, the solvent is an organic solvent. In certain embodiments, the solvent is a haloginated solvent, an ester solvent, a ketone solvent, an ether solvent, an alcohol, an aliphatic solvent, or an aromatic solvent. In one embodiment, the solvent is chloroform, dichloromethane, dichloroethane, methyl acetate, ethyl acetate, propyl acetate, butyl acetate, acetonitrile, acetone, acetic acid, dioxane, diglyme, dioxin, tetrahydrofuran, pentane, hexane, heptane, benzene, toluene, xylene, trimethylbenzene, ethylbenzene, methylethylbenzene, hexofluoroisopropanol, or any mixtures or combinations thereof. In one embodiment, the solvent is dichloromethane.

In some embodiments, the method further includes contacting the PHA and the alcohol with a base to convert at least a portion of the PHA to alkyl hydroxyalkanoate, alkyl alkenoate, or a mixture thereof. In various embodiments, the base is an organic base, a carbonate salt, an oxide salt, a hydroxide salt, a buffer, or any combinations thereof.

In yet other embodiments, the method further includes contacting the PHA and the alcohol with any of the solvents described above and any of the bases described above to convert at least a portion of the PHA to alkyl hydroxyalkanoate, alkyl alkenoate, or a mixture thereof.

In certain embodiments, the alcohol is a $C_1$-$C_{10}$ alcohol, or a $C_1$-$C_6$ alcohol, or a $C_1$-$C_4$ alcohol. In one embodiment, the alcohol is methanol, ethanol, propanol, butanol, pentanol or hexanol. In a particular embodiment, the alcohol is methanol.

In certain embodiments, the alcohol is a critical, supercritical or near-critical $C_1$-$C_{10}$ alcohol, or a critical, supercritical or near-critical $C_1$-$C_6$ alcohol, or a critical, supercritical or near-critical $C_1$-$C_4$ alcohol. In one embodiment, the alcohol is critical, supercritical or near-critical methanol; critical, supercritical or near-critical ethanol; critical, supercritical or near-critical propanol; critical, supercritical or near-critical butanol; critical, supercritical or near-critical pentanol; or critical, supercritical or near-critical hexanol. In a particular embodiment, the alcohol is critical, supercritical or near-critical methanol.

In some embodiments, the alkyl hydroxyalkanoate is alkyl 3-hydroxyalkanoate. In some embodiments, the alkyl 3-hydroxyalkanoate is methyl 3-hydroxybutanoate or methyl 3-hydroxypentanoate. In some embodiments, the alkyl alkenoate is alkyl alk-2-enoate. In some embodiments, the alkyl alk-2-enoate is methyl but-2-enoate or methyl pen-2-enoate.

In some embodiments, the PHA is provided in cell debris, cell mass, cell paste or biomass, and the cell debris, cell mass, cell paste, or biomass is contacted with the alcohol to convert at least a portion of the PHA to alkyl hydroxyalkanoate, alkyl alkenoate, or a mixture thereof. In other embodiments, the PHA is intracellular PHA, and the cell containing the PHA is contacted with the alcohol to convert at least a portion of the PHA to alkyl hydroxyalkanoate, alkyl alkenoate, or a mixture thereof. In certain embodiments, at least 10%, at least 15%, at least 20%, at least 25%, at least 30%, at least 40%, at least 50%, at least 60%, at least 70%, at least 75%, at least 80%, or at least 90% (by dry weight) of the cell debris, cell mass, cell paste or biomass in contact with the alcohol is the PHA.

In some embodiments, the PHA is polyhydroxybutyrate (PHB), polyhydroxyvalerate (PHV), polyhydroxybutyratevalerate (PHBV), or polyhydroxyhexanoate (PHH), or a combination thereof.

Provided is a method for producing alkanediol, by: a) providing alkyl hydroxyalkanoate according to any of the methods described above; and b) converting at least a portion of the alkyl hydroxyalkanoate to alkanediol.

Provided is also a method for producing alkadiene, by: a) providing alkanediol according to the method described above; and b) converting at least a portion of the alkanediol to alkadiene. The alkanediol may be produced according to any of the methods described above. In some embodiments, the alkadiene is alka-1,3-diene. In one embodiment, the alka-1,3-diene is buta-1,3-diene. In some embodiments, the alkanediol is alkane-1,3-diol. In one embodiment, the alkane-1,3-diol is butane-1,3-diol.

Provided is also a method for producing alkyl hydroxyalkenoate, by: a) providing alkyl alkenoate according to any of the methods described above; and b) converting at least a portion of the alkyl alkenoate to alkyl hydroxyalkenoate. In some embodiments, the alkyl hydroxyalkenoate is alkyl 4-hydroxyalk-2-enoate. In one embodiment, the alkyl 4-hydroxyalk-2-enoate is methyl 4-hydroxybut-2-enoate.

Provided is also a method for producing alkenedioic acid, by: a) providing alkyl hydroxyalkenoate according to any of the methods described above; and b) converting at least a portion of the alkyl hydroxyalkenoate to alkenedioic acid. In some embodiments, the alkenedioic acid is butenedioic acid. In one embodiment, the butenedioic acid is 2-butenedioic acid.

In another aspect, provided is a method for producing alkadiene, by: a) providing PHA; b) providing an alcohol; c) contacting the PHA with the alcohol to convert at least a portion of the PHA to alkyl hydroxyalkanoate; and d) converting at least a portion of the alkyl hydroxyalkanoate to alkadiene. In some embodiments, the converting of at least a portion of the alkyl hydroxyalkanoate to alkadiene includes: i) converting at least a portion of the alkyl hydroxyalkanoate to alkanediol; and ii) converting at least a portion of the alkanediol to alkadiene. In some embodiments, the alkyl hydroxyalkanoate is alkyl 3-hydroxyalkanoate. In one embodiment, the alkyl 3-hydroxyalkanoate is methyl 3-hydroxybutanoate. In some embodiments, the alkyl alkenoate is alkyl alk-2-enoate. In one embodiment, the alkyl alk-2-enoate is methyl but-2-enoate. In some embodiments, the alkadiene is alka-1,3-diene. In one embodiment, the alka-1,3-diene is buta-1,3-diene. In some embodiments, the alkanediol is alkane-1,3-diol. In one embodiment, the alkane-1,3-diol is butane-1,3-diol.

Provided is also a method for producing butadiene, by: a) providing PHA; b) providing methanol; c) contacting the PHA with the methanol to convert at least a portion of the PHA to methyl 3-hydroxybutanoate; d) converting at least a portion of the methyl 3-hydroxybutanoate to butanediol; and e) converting at least a portion of the butanediol to butadiene.

Provided is a method for producing alkenedioic acid, by: a) providing PHA; b) providing alkanol; c) contacting the PHA with the alkanol to convert at least a portion of the PHA to alkyl alkenoate; and d) converting at least a portion of the alkyl alkenoate to alkenedioic acid. In some embodiments, the converting of at least a portion of the alkyl alkenoate to alkenedioic acid includes: i) converting at least a portion of the alkyl alkenoate to alkyl hydroxyalkenoate; and ii) converting at least a portion of the alkyl hydroxyalkenoate to alkenedioic acid. In some embodiments, the alkenedioic acid is butenedioic acid. In some embodiments, the alkyl alkenoate is alkyl alk-2-enoate. In one embodiment, the alkyl alk-2-enoate is methyl but-2-enoate. In some embodiments, the alkyl hydroxyalkenoate is alkyl 4-hydroxyalk-2-enoate. In one embodiment, the alkyl 4-hydroxyalk-2-enoate is methyl 4-hydroxybut-2-enoate.

Provided is also a method for producing butenedioic acid, by: a) providing PHA; b) providing methanol; c) contacting the PHA with the methanol to convert at least a portion of the PHA to methyl but-2-enoate; d) converting at least a portion of the methyl but-2-enoate to methyl 4-hydroxybut-2-enoate; and e) converting at least a portion of the methyl 4-hydroxybut-2-enoate to butenedioic acid.

DESCRIPTION OF THE FIGURES

The present application can be best understood by reference to the following description taken in conjunction with the accompanying figures, in which like parts may be referred to by like numerals.

FIG. 1a depicts an exemplary reaction for converting PHB into methyl 3-hydroxybutanoate (Compound I) and methyl but-2-enoate (Compound II). FIG. 1b depicts an exemplary reaction for converting methyl 3-hydroxybutanoate (Compound I) to butadiene (Compound IV), through butanediol (Compound III). FIG. 1c depicts an exemplary reaction for converting methyl but-2-enoate (Compound i) to butenedioic acid (Compound VI), through methyl 4-hydroxybut-2-enoate (Compound V).

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are methods for producing various polyhydroxyalkanoate (PHA) derivatives. Compounds that can be prepared directly from PHAs are generally depicted in Scheme 1 below.

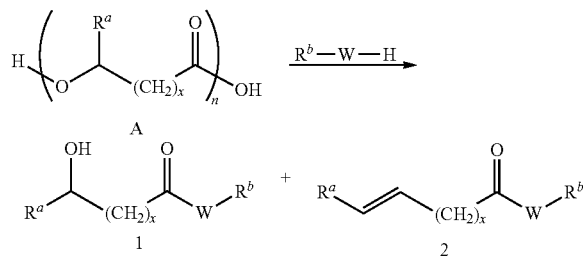

Scheme 1

The PHA of Formula A provided in Scheme 1 is described in further detail below. The nucleophile provided in Scheme 1 has a Formula of $R^b$—W—H, where W can be O, N, or S. It should be understood that while primary alcohols, amines and thiols are depicted as the nucleophile in exemplary Scheme 1, the nucleophile may be a second or tertiary alcohol, amine, or thiol. It should be further understood that structures of compounds of Formulae 1 and 2 will depend on the PHA and the nucleophile used.

Figure 1:
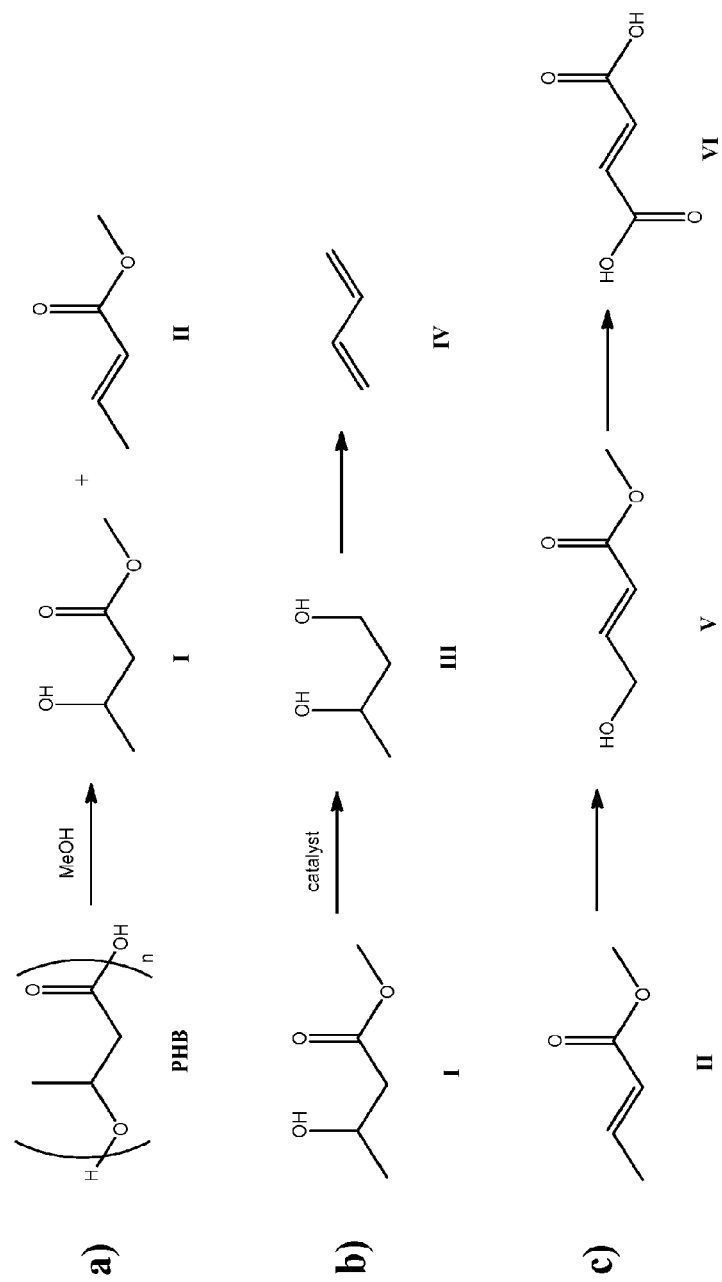
FIG. 1 depicts an exemplary reaction scheme for converting polyhydroxybutyrate (PHB) into butadiene (Compound IV) and butenedioic acid (Compound VI). In particular.

Provided herein are also methods for producing other PHA derivatives from the compounds of Formulae 1 and 2. For example, when the compound of Formula 1 is methyl 3-hydroxybutanoate, this compound may be used to prepare butanediol and butadiene. When the compound of Formula 2 is methyl but-2-enoate, this compound may be used to prepare methyl 4-hydroxybut-2-enoate and butenedioic acid. The reaction schemes to produce these PHA derivatives are exemplified in FIG. 1.

The PHAs used to prepare the PHA derivatives described above, and the methods to prepare such derivatives are further described in detail below.

Polyhydroxyalkanoates (PHAs)

The methods described herein utilize PHAs for conversion into various compounds. PHAs are linear polyesters that can be produced by fermentation of sugar and/or lipids. Providing a PHA, as described in the methods herein, may include producing the PHA, or obtaining the PHA from any source (including commercially available sources).

One of skill in the art would recognize that PHAs can be produced from a variety of monomers and molecular weights, with assembly performed by bacteria, yeast, and plants. See Tsuge et al., *Macromolecular Bioscience* 7.6 (2007): 846-54; Tsuge, et al., *Macromolecular Bioscience* 5.2 (2005): 112-17; Abd-El-Haleem, Desouky AM., *Polish Journal of Microbiology* 58.1 (2009): 37-41; Poirier, Y., *Current Opinion in Biotechnology* 10.2 (1999): 181-85. PHA production can be based on renewable resources as opposed to diminishing fossil fuel stockpiles. For example, PHAs can be commercially produced in bacterial fermentation processes using substrates to drive microorganism growth and PHA synthesis. These substrates may include be, for example, agricultural products such as sugars and fatty acids.

Suitable bacteria used for fermentation of a feedstock to produce PHAs may include a strain selected from, for example, *Delftia*, *Pseudomonas*, and *Cupriavidus*. In some embodiments, the bacterial strain may include *Delftia acidovorans*, *Pseudomonas fuscovaginae*. *Pseudomonas pseudoalcaligenes*, *Pseudomonas putida*, *Pseudomonas aeruginosa*, and *Cupriavidus necator*. Suitable genetically-engineered organisms known in the art may also be used for fermentation of a feedstock to produce PHAs.

In some embodiments, providing a PHA involves providing a fermentation product mixture containing a PHA. It should be understood that the fermentation product mixture containing a PHA may be obtained from any source (including any commercially available sources) or methods known in the art. In one embodiment, the PHA may be isolated from the fermentation product mixture, and optionally may be further purified. Any suitable isolation and purification techniques known in the art may be used. In another embodiment, the fermentation product mixture containing a PHA may be used without isolating and/or purifying the PHA.

In other embodiments, providing a PHA involves providing a PHA embedded in cell debris, cell mass, cell paste, or biomass. In other embodiments, the PHA may be intracellular PHA. In certain embodiments, the PHA is at least 10%, at least 15%, at least 20%, at least 25%, at least 30%, at least 40%, at least 50%, at least 60%, at least 70%, at least 75%, at least 80%, or at least 90% (by dry weight) of the total substrate that is in contact with the nucleophile (e.g. the alcohol, the amine, or the thiol).

In some embodiments, the PHAs have a structure of Formula A:

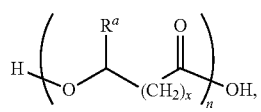
(A)

in which $R^a$ is an aliphatic group; x is an integer greater than or equal to 1; and n is an integer greater than or equal to 20. In some embodiments, x is 1 to 50; 1 to 20; or 1 to 10. In some embodiments, n is 50 to 100.000; 100 to 30.000; or 1.000 to 10,000.

The aliphatic group may include, for example, compounds made up of carbon and hydrogen atoms that are non-aromatic. The aliphatic group may be straight-chained or branched. The aliphatic group may also be cyclic. The aliphatic group may also be saturated (e.g., alkyl) or unsaturated (e.g., alkenyl or alkynyl).

In some embodiments, $R^a$ is alkyl, alkenyl, or alkynyl In certain embodiments, $R^a$ is alkyl. In certain embodiments, $R^a$ is $C_1$-$C_{20}$ alkyl. In some embodiments, $R^a$ is $C_1$-$C_6$ alkyl. In one embodiment, $R^a$ is methyl (i.e., a $C_1$ alkyl) or ethyl (i.e., a $C_2$ alkyl). In other embodiments, x is 1 to 9; 1 to 8; 1 to 7; 1 to 6; 1 to 5; 1 to 4; 1 to 3; or 2 or 1. In one embodiment, x is 1. In one embodiment, $R^a$ is methyl and x is 1 (i.e., the PHA is polyhydroxybutyrate). In another embodiment, $R^a$ is ethyl and x is 1 (i.e., the PHA is polyhydroxyvalerate). In other embodiments, $R^a$ may be any aliphatic group, which may vary depending on the feedstock used to produce the PHAs.

As used herein. "alkyl" is a saturated straight-chain or branched-chain monovalent hydrocarbon group, which contains only C and H when unsubstituted. Examples include methyl, ethyl, propyl, butyl and pentyl. When an alkyl residue having a specific number of carbons is named, all geometric isomers having that number of carbons are intended to be encompassed and described; thus, for example, "butyl" is meant to include n-butyl, see-butyl, iso-butyl, and tert-butyl; "propyl" includes n-propyl, and iso-propyl. The total number of carbon atoms in each such group is sometimes described herein. For example, when the group can contain up to five carbon atoms it can be represented as 1-5C or as $C_1$-$C_5$ or $C_{1-5}$. In certain embodiments, alkyl may include cycloalkyl.

As used herein, "alkenyl" refers to an unsaturated hydrocarbon group having at least one site of olefinic unsaturation (i.e., having at least one moiety of the Formula C═C). Alkenyl contains only C and H when unsubstituted. When an alkenyl residue having a specific number of carbons is named, all geometric isomers having that number of carbons are intended to be encompassed and described; thus, for example, "butenyl" is meant to include n-butenyl, sec-butenyl, and iso-butenyl. Examples of alkenyl may include —CH═CH₂, —CH₂—CH═CH₂ and —CH₂—CH═CH—CH═CH₂. In certain embodiments, alkenyl may include cycloalkenyl.

As used herein, "alkynyl" refers to "an unsaturated hydrocarbon group having at least one site of acetylenic unsaturation (i.e., having at least one moiety of the Formula C≡C. Alkynyl contains only C and H when unsubstituted. When an alkynyl residue having a specific number of carbons is named, all geometric isomers having that number of carbons are intended to be encompassed and described; thus, for example, "pentynyl" is meant to include n-pentynyl, sec-pentynyl, iso-pentynyl, and tert-pentynyl. Examples of alkynyl may include —C≡CH or —C≡C—CH₃. In certain embodiments, alkynyl may include cycloalkynyl.

Although Formula A above depicts a PHA polymer, it should be understood that the PHAs provided as the substrate for producing one or more derivative compounds may be co-polymers. For example, the PHAs may be polymers and/or co-polymers including polyhydroxybutyrate (PHB), polyhydroxyvalerate (PHV), polyhydroxyhexanoate (PHH), polyhydroxyoctanoate (PHO), polyhydroxydecanoate, and polyhydroxybutyratevalerate (PHBV). It should be understood that the blend of polymers and/or co-polymers may include straight-chained or branched PHAs that may be substituted with different functional groups.

The PHA used in the methods described herein may be a mixture or blend. For example, as discussed above, the PHA may be produced by fermentation of a feedstock. The resulting fermentation product mixture may include a mixture of PHAs or co-polymers, based on the starting material and bacteria strains used. In some embodiments, the PHA used in the methods described herein may include a blend of PHB and PHV. In certain embodiments. PHB may be present in excess of PHV. For example, the PHA may include a 90:10 ratio, an 85:15 ratio, an 80:20 ratio, or a 70:30 ratio of PHB to PHV. In other embodiments, PHV may be present in excess of PHB. For example, the PHA may include a 90:10 ratio, an 85:15 ratio, an 80:20 ratio, or a 70:30 ratio of PHV to PHB.

PHA Derivatives of Scheme 1

Scheme 1 above describes a general reaction scheme to produce PHA derivatives of Formulae 1 and 2. As discussed above, the nucleophile used in this reaction may be an alcohol, an amine, or a thiol. In some embodiments, the reaction may be performed at critical, supercritical or near-critical conditions, or the nucleophile provided may be a critical, supercritical or near-critical nucleophile. Such conditions for the reaction are discussed in further detail below.

Alcohol as Nucleophile—Production of Alkyl Hydroxyalkanoates and Alkyl Alkenoates In some embodiments, when the nucleophile is an alcohol, the PHAs may be used to produce alkyl hydroxyalkanoates and/or alkyl alkenoates. The alcohol may have at least one hydroxyl (—OH) group. For example, the nucleophile may be an alkanol. As used herein, "alkanol" refers to an alkyl having at least one hydroxyl group.

Scheme 1a below depicts an exemplary reaction scheme to produce alkyl hydroxyalkanoates and alkyl alkenoates from a PHA having a structure of Formula A using a nucleophile of Formula B. As depicted in Scheme 1a, PHAs can undergo esterification in the presence of a nucleophile to produce alkyl hydroxyalkanoates, alkyl alkenoates, or a mixture thereof. In some embodiments, when the nucleophile has a structure of Formula B, an alkyl hydroxyalkanoate having the structure of Formula C and an alkyl alkenoate having the structure of Formula D may be produced. It should be understood that $R^a$ and x in Formulae C and D are as defined for the Formula A, and $R^b$ will depend on the nucleophile used, as discussed in further detail below.

Scheme 1a

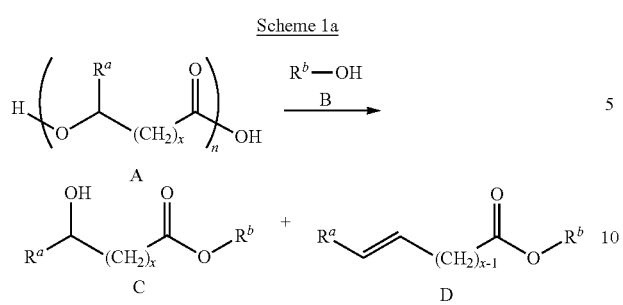

In certain embodiments, $R^b$ is alkyl. In some embodiments, $R^b$ is $C_1$-$C_{20}$ alkyl, $C_1$-$C_{10}$ alkyl, or $C_1$-$C_6$ alkyl. In one embodiment, $R^b$ is methyl (i.e., the nucleophile is methanol) or ethyl (i.e., the nucleophile is ethanol). Other suitable alcohols may include, for example, propanol, butanol, pentanol, and hexanol.

While a primary alcohol (e.g., $R^b$ is a linear alkyl) is depicted as the nucleophile of Formula B, it should be understood that, in other exemplary embodiments, the nucleophile may be a secondary alcohol or a tertiary alcohol (e.g., $R^b$ is a branched alkyl).

Figure 3:
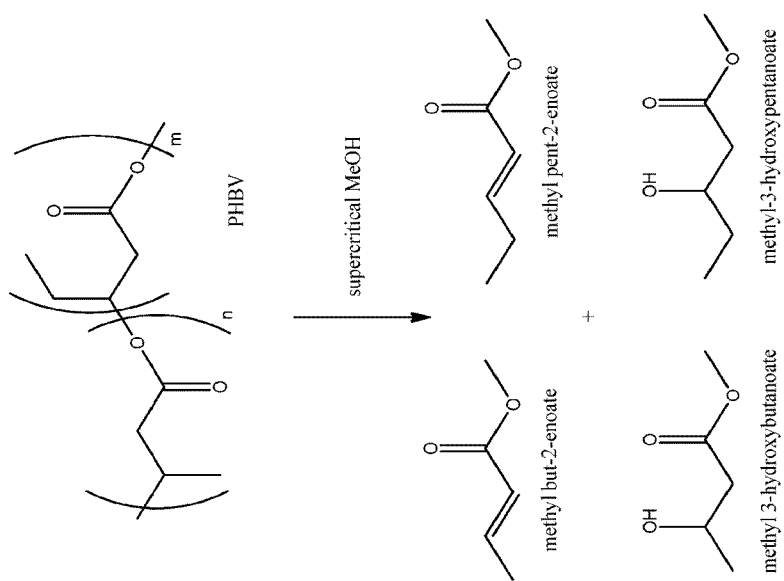
FIG. 3 depicts an exemplary reaction involving the production of methyl 3-hydroxybutanoate, methyl but-2-enoate, methyl-3-hydroxypentanoate and methyl pent-2-enoate from polyhydroxybutyratevalerate (PHBV) and supercritical methanol as the nucleophile.

It should further be understood that when the PHAs provided for this reaction is a copolymer with different types of monomeric units, a mixture of compounds C and a mixture of compounds D may be produced. For example, with reference to FIG. 3, when the PHA is polyhydroxybutyratevalerate (PHBV), a mixture of methyl 3-hydroxybutanoate, methyl but-2-enoate, methyl-3-hydroxypentanoate and methyl pent-2-enoate may be produced.

In one aspect, provided herein are also compositions that include methyl 3-hydroxybutanoate, methyl but-2-enoate, methyl-3-hydroxypentanoate, and methyl pent-2-enoate. In certain embodiments, the compositions further include polyhydroxybutyratevalerate and methanol. In one embodiment, provided is a composition that includes methyl 3-hydroxybutanoate, methyl but-2-enoate, methyl-3-hydroxypentanoate, methyl pent-2-enoate, and a critical, supercritical or near-critical alcohol (e.g., methanol).

Amine as Nucleophile

With reference to Scheme 1b below, in other embodiments, when the nucleophile is an amine, the PHAs may be used to produce PHA derivatives, such as, compounds of Formula C" and D'.

Scheme 1b

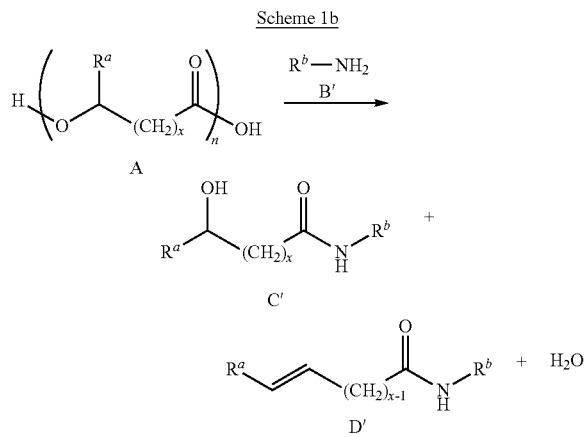

In certain embodiments, R is alkyl. In some embodiments, $R^b$ is $C_1$-$C_{20}$ alkyl, $C_1$-$C_{10}$ alkyl, or $C_1$-$C_6$ alkyl. In one embodiment, $R^b$ is methyl or ethyl.

While a primary amine is depicted, in other embodiments, the amine may be a secondary amine or a tertiary amine. For example, secondary amines may have the formula $R^b$—NHR', or $R^b$—NR'R", where each R' and R" may independently be an aliphatic group, such as an alkyl.

Thiol as Nucleophile

With reference to Scheme 1c below, in yet other embodiments, when the nucleophile is a thiol, the PHAs may be used to produce PHA derivatives, such as, compounds of Formula C" and D".

Scheme 1c

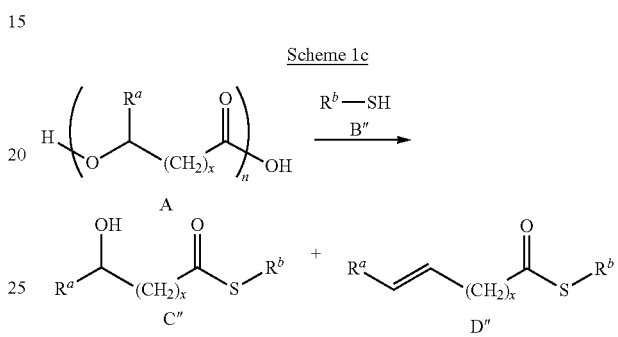

In certain embodiments, $R^b$ is alkyl. In some embodiments, $R^b$ is $C_1$-$C_{20}$ alkyl, $C_1$-$C_{10}$ alkyl, or $C_1$-$C_6$ alkyl. In one embodiment, $R^b$ is methyl or ethyl.

Reaction Conditions

The PHAs provided may undergo esterification in the presence of a nucleophile at any temperature and/or pressure suitable for converting at least a portion of the PHAs into one or more PHA derivatives (e.g., compounds of Formulae C and D, or C' and D' or C" and D", depending on the nucleophile used). For example, the PHAs may undergo esterification in the presence of an alcohol at any temperature and/or pressure suitable for converting at least a portion of the PHAs into alkyl hydroxyalkanoates, alkyl alkenoates, or a mixture thereof.

In some embodiments, the reaction temperature is between 150° C. and 350° C., between 180° C. and 320° C., between 220° C. and 300° C., or between 240° C. and 260° C. In some embodiments, the reaction pressure is between 500 psi and 3000 psi, between 800 psi and 3000 psi, between 1000 psi and 2000 psi, between 1000 psi and 1600 psi, or between 1200 psi and 1500 psi.

It should be understood that any of the reaction temperatures described herein may be combined with any of the pressures described herein, as if each and every combination were listed separately. For example, in one embodiment, the reaction temperature is between 150° C. and 350° C., and the reaction pressure is between 1000 psi and 3000 psi. In another embodiment, the reaction temperature is between 200° C. and 300° C., and the reaction pressure is between 600 psi 3000 psi. It should be further understood, however, that in some embodiments, certain temperatures and pressures may be combined to achieve critical, supercritical or near-critical conditions as further described below.

The nucleophile may be provided at standard temperature and pressure when initially contacted with the PHA, and the temperature and/or pressure of the reaction system may subsequently be increased to a temperature and/or pressure suitable for converting at least a portion of the PHA into one or more PHA derivatives. For example, in certain embodiments, the alcohol may be provided at standard temperature and pressure when initially contacted with the PHA, and the temperature and/or pressure of the reaction system may subsequently be increased to a temperature and/or pressure suitable for converting at least a portion of the PHA into alkyl hydroxyalkanoates, alkyl alkenoates, or a mixture thereof.

In one embodiment, the nucleophile may be fed into a reactor at standard temperature and pressure, and the temperature may be increased to between 150° C. and 350° C. and/or the pressure may be increased to between 1000 psi and 3000 psi. In another embodiment, the nucleophile may be provided at standard temperature and pressure when initially contacted with the PHA, and the temperature and/or pressure of the reaction system may subsequently be increased to critical, supercritical or near-critical conditions.

Supercritical and near-critical conditions depend on the critical point of a reaction system, which can vary depending on the nucleophile used. The critical point of a reaction system is a combination of temperature and pressure above which distinct liquid and gas phases do not exist. Critical temperature is the temperature of the reaction system at the critical point. Critical pressure is the pressure of the reaction system at the critical point. Measurements of the critical temperature and critical pressure of the reaction systems described herein to produce the PHA derivatives (e.g., of exemplary Scheme 1) may vary depending on the measurement methods, techniques, tools and/or systems used. For example, the term "about" when used in association with the critical temperature may refer to variations of +/−30° C. depending on how temperature is measured. Similarly, the term "about" when used in association with the critical pressure may refer to variations of +/−20 psi depending on how pressure is measured. In all other instances, unless otherwise specified, the term "about" when used in association with other measurements, or used to modify a value, a unit, a constant, or a range of values, refers to variations of +/−5%. It should also be understood that reference to "about" a value or parameter herein includes (and describes) embodiments that are directed to that value or parameter per se. For example, description referring to "about x" includes description of "x" per se.

Figure 2:
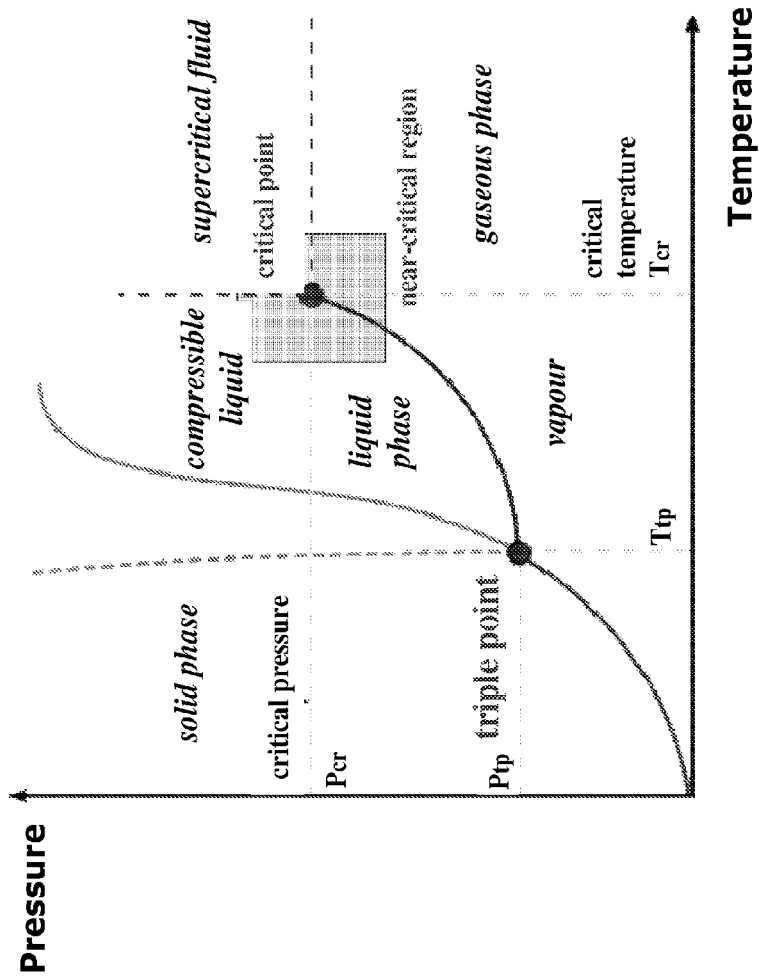
FIG. 2 depicts a phase diagram showing the regions of temperature and pressure at which the various phases exist and where phase changes occur.

With reference to FIG. 2, supercritical conditions refer to temperatures and pressures above the critical point. In some embodiments, supercritical conditions refer to the conditions at which the nucleophile does not exist as distinct liquid and gas phases. For example, if the nucleophile had a critical point at about 240° C. and about 1170 psi, then the supercritical conditions for that nucleophile may involve temperatures above about 240° C. and pressures above about 1170 psi. In certain embodiments, the supercritical conditions for the nucleophile from this example may involve temperatures between about 240° C. and about 260° C., and pressures between about 1170 psi and about 1300 psi. It should be understood that the supercritical nature of the reaction system may be achieved by either (i) providing the nucleophile at supercritical conditions, or (ii) adjusting the temperature and/or pressure of the reaction system so that the nucleophile is a supercritical fluid in the reaction system, or a combination thereof.

With reference again to FIG. 2, near-critical refers to temperatures and/or pressures that are slightly below the critical point. In some embodiments, near-critical refers to temperatures that are up to about 10% more than the critical temperature and up to about 30% less than the critical pressure; or temperatures that are up to about 10% less than the critical temperature and up to about 30% more than the critical pressure; or temperatures that are up to about 10% less than the critical temperature and up to about 30% less than the critical pressure. For example, if the nucleophile had a critical point at 240° C. and 1170 psi, then the near-critical conditions for the nucleophile may involve a temperature between 210° C. and 240° C. and a pressure between 880 psi and 1170 psi; or a temperature between 220° C. and 240° C. and a pressure between 1000 psi and 1170 psi. It should be understood that the near-critical nature of the reaction may be achieved by either (i) providing the nucleophile at near-critical conditions, or (ii) adjusting the temperature and/or pressure of the reaction system so that the nucleophile is a near-critical fluid in the reaction system, or a combination thereof.

In some embodiments, the residence time may also be varied depending on the reaction temperature and/or pressure. For example, in certain embodiments, the PHA is contacted with the nucleophile for a residence time of less than 48 hours, 24 hours, 16 hours, 12 hours, 6 hours, 4 hours, 2 hours, 1 hour, 30 minutes, 20 minutes, 15 minutes, 10 minutes, 5 minutes, 1 minute, or 30 seconds.

Solvent

In some embodiments, the nucleophile described above may act as the solvent for the reaction system. In other embodiments, a solvent or a mixture of solvents may be added to the reaction system. If a solvent or mixture of solvents are added, such solvents provided to the reaction may be obtained from any source, including any commercially available sources.

With reference to Scheme 1, the PHA may be contacted with the nucleophile in the presence of a solvent or a mixture of solvents to convert at least a portion of the PHA to compounds of Formulae C and D. In a particular example, the PHA may be contacted with the alcohol in the presence of a solvent or a mixture of solvents to convert at least a portion of the PHA to alkyl hydroxyalkanoate, alkyl alkenoate, or a mixture thereof. It should be understood that the solvent selected may depend on the nucleophile used. For example, when the nucleophile is methanol, an ester solvent may be used such as methyl acetate.

Suitable solvents may include any solvent that can dissolve PHA, partially dissolve PHA, or improve PHA solubility of the reaction system. The solvent may be an organic solvent. The solvent may be a haloginated solvent, an ester solvent, a ketone solvent, an ether solvent, an alcohol solvent, an aliphatic solvent, or an aromatic solvent. It should be understood that the solvent may fall within one or more classes of solvents described above.

In certain embodiments, the solvent may be haloginated, referring to a solvent having at least one halo group. For example, the halogenated solvent may be aliphatic substituted with one or more halo groups. In one embodiment, the solvent is a chlorinated solvent, such as tetrachloride, chloroform and dichloromethane.

In certain embodiments, the solvent may be an ester, which refers to a solvent having at least one ester group. For example, the ester solvent may be alkyl acetate (e.g., methyl acetate, ethyl acetate, propyl acetate, butyl acetate). It should be understood, however, that a solvent having an ester group may also have one or more other functional groups. For example, an ester solvent may be alkyl lactate (e.g., methyl lactate, ethyl lactate, propyl lactate, butyl lactate), which has both an ester group as well as a hydroxyl group.

In other embodiments, the solvent may be an ether, which refers to a solvent having at least one ether group. An ether solvent can be non-cyclic or cyclic. For example, the ether solvent may be alkyl ether (e.g., diethyl ether, glycol dimethyl ether (glyme), diethylene glycol dimethyl ether (diglyme), or triethylene glycol dimethyl ether (triglyme)). In another example, the ether solvent may be cyclic, such as dioxane (e.g., 1,4-dioxane), dioxin, or tetrahydrofuran. The solvent may also be a polyether with two or more oxygen atoms. Examples of polyethers may include glyme, diglyme, triglyme, or tetraglyme. It should also be understood that a solvent having an ether group may also have one or more other functional groups.

In yet other embodiments, the solvent may be a ketone, which refers to a solvent having at least one carbonyl group. For example, the ketone solvent may be acetone.

In yet other embodiment, the solvent may be an alcohol. It should be understood, however, that when the nucleophile is an alcohol, the nucleophile itself may act as a solvent.

In yet other embodiments, the solvent may be an aliphatic solvent. The aliphatic solvent may be linear, branched, or cyclic. The aliphatic solvent may also be saturated (e.g., alkane) or unsaturated (e.g., alkene or alkyne). For example, the aliphatic solvent may be pentane, hexane, or heptane.

In yet other embodiments, the solvent may be an aromatic solvent. The aromatic solvent may be optionally substituted. For example, the aromatic solvent may be benzene, toluene, xylene, trimethylbenzene, ethylbenzene, and methylethylbenzene.

In particular embodiments, the solvent is chloroform, dichloromethane, dichloroethane, methyl acetate, ethyl acetate, propyl acetate, butyl acetate, acetonitrile, acetone, acetic acid, dioxane, diglyme, dioxin, tetrahydrofuran, pentane, hexane, heptane, benzene, toluene, xylene, trimethylbenzene, ethylbenzene, methylethylbenzene, hexofluoroisopropanol, or any mixtures or combinations thereof. In one embodiment, the solvent is dichloromethane.

Base

In some embodiments, the PHA may be contacted with the nucleophile and a base to convert at least a portion of the PHA to one or more PHA derivatives. For example, the PHA may be contacted with the nucleophile and a base to convert at least a portion of the PHA to alkyl hydroxyalkanoate, alkyl alkenoate, or a mixture thereof.

The base may be an organic base. Suitable organic bases include, for example, trialkylamines (e.g., triethylamine) and 1,8-diazabicycloundec-7-ene. The base may also be a salt, such as a carbonate salt, an oxide salt, or a hydroxide salt. For example, in one embodiment, the base is calcium carbonate, calcium oxide, sodium hydroxide, or a combination thereof. The base may also be a buffer. Suitable buffers include, for example, trisodium/disodiumphosphate, or acetate/acetic acid. A combination of bases may also be used.

In other embodiments, the PHA may be contacted with the nucleophile in the presence of a suitable solvent described above and a suitable base described above.

Products

With reference to Scheme 1 above, the products include compounds of Formulae C and D. In a particular example, with reference to Scheme 1a above, when the nucleophile is alcohol, alkyl hydroxyalkanoates and alkyl alkenoates may produced from the esterification reaction. The particular alkyl hydroxyalkanoates and alkyl alkenoates produced may vary depending on the PHA and the nucleophile used.

For example, in one embodiment where the PHA is polyhydroxybutyrate or a copolymer that contains polyhydroxybutyrate, trans-esterification of polyhydroxybutyrate in the presence of methanol as the nucleophile may produce methyl 3-hydroxybutanoate and methyl but-2-enoate. In other embodiments where the PHA is polyhydroxyvalerate or a copolymer that contains polyhydroxyvalerate, trans-esterification of polyhydroxyvalerate in the presence of methanol as the nucleophile may produce methyl 3-hydroxypentanoate and methyl pent-2-enoate. If the PHA is a blend of polyhydroxybutyrate and polyhydroxyvalerate, then a mixture of one or more alkyl hydroxyalkanoates and one or more alkyl alkenoates may be produced depending on the reaction conditions. For example, a mixture of methyl 3-hydroxybutanoate, methyl but-2-enoate, methyl 3-hydroxypentanoate and methyl pent-2-enoate may be produced.

The ratio of the alkyl hydroxyalkanoate and alkyl alkenoate produced from the esterification reaction described herein may vary depending on the reaction conditions, including for example temperature and reaction time. In some embodiments, alkyl hydroxyalkanoate may be produced in excess of the alkyl alkenoate. For example, alkyl hydroxyalkanoate and alkyl alkenoate may be produced in a ratio of 1-5 to 1, or 1-3 to 1. In other embodiments, alkyl alkenoate may be produced in excess of the alkyl hydroxyalkanoate. For example, alkyl hydroxyalkanoate and alkyl alkenoate may be produced in a ratio of 1 to 1-5, or 1 to 1-3.

Other PHA Derivatives

Production of Alkadienes from Alkyl Hydroxyalkanoates

In some embodiments, the alkyl hydroxyalkanoates produced from PHAs according to the methods described above may be used in the synthesis of alkadienes. Scheme 2a below depicts an exemplary reaction scheme to reduce alkyl hydroxyalkanoates to form alkanediols, which can undergo dehydration to yield alkadienes. In some embodiments, an alkanediol has the structure of Formula E, and an alkadiene has the structure of Formula F. It should be understood that $R^a$ and x in Formulae E and F are as defined in Formula A.

Scheme 2a

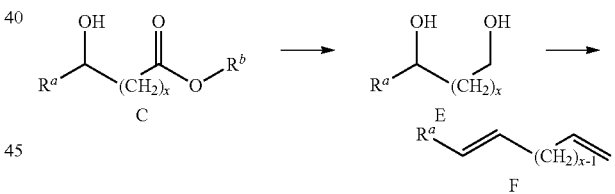

Reduction of Alkyl Hydroxyalkanoate to Produce Alkanediol

The conversion of an alkyl hydroxyalkanoate of Formula C can be converted into an alkanediol of Formula E by the reduction of the ester group in the alkyl hydroxyalkanoate to an alcohol group in the alkanediol. Suitable reaction conditions are known in the art. For example, methyl 3-hydroxybutanoate may be reacted with $H_2$ (4 MPa) in the presence of a ruthenium catalyst, e.g., $RuH(\eta^1\text{-}CH4)(dppp)$ (dpen), at 80° C. for 16 hours to yield 1,3-butanediol. See Ino et al., *Top Catal* (2010) 53:1019-1024.

In other embodiments, alkanediol can be produced from PHAs in a one-pot reaction. Scheme 2b below is an exemplary reaction scheme that depicts the production of alkanediol from a PHA through an alkyl hydroxyalkanoate intermediate.

Scheme 2b

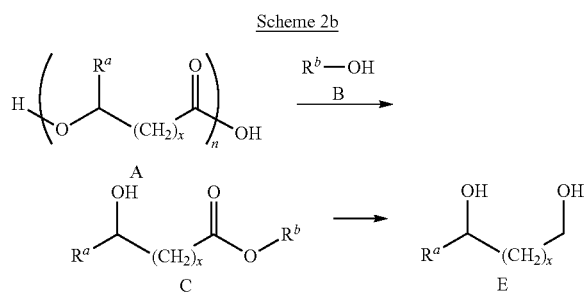

Dehydration of Alkanediol to Alkadiene

With reference to Scheme 2a above, alkanediol of Formula E may be dehydrated under suitable conditions known in the art to produce alkadiene of Formula F, such as 1,3-butadiene. For example, 1,3-butanediol may be dehydrated in the gas phase at 270° C. with a sodium polyphosphate catalyst. See e.g., Industrial Organic Chemistry, 5$^{th}$ ed., Wiley-Vch Verlag GmbH & Co. KgaH (2010), p. 108.

Production of Alkenedioic Acid from Alkyl Alkenoate

The alkyl alkenoate produced from the PHAs according to the methods described above may be used in the synthesis of alkenedioic acid. Scheme 3 below depicts an exemplary reaction Scheme 1n which the alkyl alkenoate is converted an alkyl hydroxyalkenoate, which can be subsequently converted into alkenedioic acid. In some embodiments, an alkyl hydroxyalkenoate has the structure of Formula G, and an alkenedioic acid has the structure of Formula H. It should be understood that x in Formulae G and H are as defined in Formula A.

Scheme 3

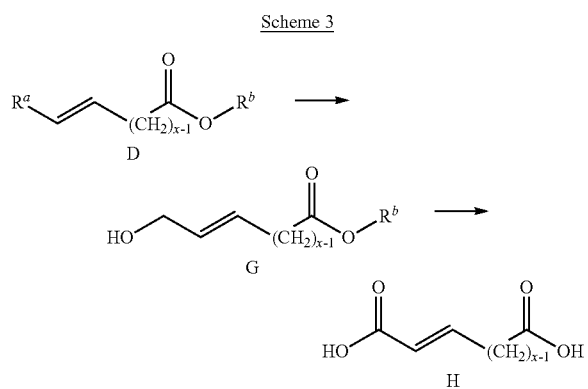

For example, in one embodiment, methyl but-2-enoate produced from PHAs can be converted to methyl 4-hydroxybut-2-enoate, and which can subsequently be converted to butenedioic acid.

The alkyl alkenoate of Formula D can be converted into an alkenedioic acid of Formula G by any suitable methods known in the art. For example, methyl but-2-enoate can be reacted with selenium dioxide ($SeO_2$) to produce methyl 4-hydroxybut-2-enoate. See e.g., Riaz et al., *Tet. Letters* 45 (2004) 293-294.

The alkenedioic acid of Formula G can be converted into an alkenedioic acid of Formula H by any suitable methods known in the art. For example, methyl 4-hydroxybut-2-enoate can be reacted with chromium (III) oxide, sulfuric acid and acetone to produce butenedioic acid. See e.g., Eisenfuhr et al., *Bioorganic & Medicinal Chemistry*, 11 (2003) 235-294.

Downstream Chemical Products

The alkadiene and alkenedioic acid produced according to the methods described herein may be used to produce various industrial chemicals or compounds, including plastics, rubbers, coatings, additives, fuels and pharmaceuticals.

For example, butadiene can be polymerized to produce synthetic rubber. Examples of such rubbers prepared from butadiene as a building block include acrylonitrile butadiene styrene (ABS), acrylonitrile butadiene (NBR) and styrene-butadiene (SBR).

Butenedioic acid can be found as the cis-isomer (i.e., maleic acid) or as the trans-isomer (i.e., fumaric acid). Maleic acid can be converted to fumaric acid using any processes known in the art. Fumaric acid may be used as a building block for pharmaceutical compounds, as well as food additives.

EXAMPLES

The compounds described herein may be prepared by a number of processes as generally described above and more specifically in the Examples hereinafter.

Where it is desired to obtain a particular isomer of a compound, this may be accomplished from a corresponding mixture of isomers using any suitable conventional procedure for separating or resolving isomers. Thus, for example, cis- and trans-isomers may be produced in a reaction, and such isomers may then be separated by any convenient means, for example by column chromatography or crystallization. Alternatively, if desired a particular isomer may be obtained by using an appropriate intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: Automation and Control Solutions (ACS); gas chromatography mass spectrometry (GCMS); high performance liquid chromatography (HPLC).

Example 1

Preparation of methyl 3-hydroxybutanoate, methyl but-2-enoate, methyl-3-hydroxypentanoate and methyl pent-2-enoate

The PHA used in this Example was a blend of polyhydroxybutyrate and polyhydroxyvalerate (80:20 PHB:PHV). The PHA produced was extracted from a fermentation mixture using dichloromethane, purified by methanol precipitation, and vacuum dried.

Approximately 5.0 g of this purified PHA was added to an open high-pressure reactor with stirring capability (Parr Instruments, Model 4520) and placed in a glove bag under argon atmosphere. 500 mL of methanol was poured into the reactor vessel. The methanol used in this Example was obtained from Honeywell ACS/HPLC Lot No: DF317 (0.032% water). The reactor lid was then placed onto the vessel and the system was sealed. The closed reactor was then removed from the inert atmosphere of the glove bag and placed in its corresponding stand where necessary heating and stirring connections were made. The stirring rate and temperature were controlled using a separate module (Parr Instruments Model 4848 Controller). After heating for approximately one hour, the system reached its temperature set point and the solution was allowed to react for an additional specified time (temperature, pressure and reaction time are summarized in Table 1 below). The reaction was repeated three times using the amount of materials and conditions set forth in Table 1 below.

TABLE 1

| Reaction # | Mass PHA (g) | Running Temperature (° C.) | Running Pressure (psig) | Reaction Time (min) |
|---|---|---|---|---|
| 1 | 5.05 | 250 | 1520 | 20 |
| 2 | 5.03 | 240 | 1150 | 1 |
| 3 | 5.01 | 230 | 1000 | 1 |

The heating module was then removed and the reactor was chilled by submersing it in an ice/water bath. Once the reactor reached room temperature, the system was opened. The reaction solution (about 500 mL) was poured into a 1 L volumetric flask. The reactor wetted parts were thoroughly rinsed with dichloromethane, which was collected in the same 1 L volumetric flask to achieve a final solution volume of 1 L. This solution was then mixed, and a sample was obtained for analysis by GCMS using the following protocol.

GC Analysis:

2 uL sample was injected onto the Agilent 6890 with MS detection at a 50:1 split ratio and flow rate of 1.1 mL/min of Helium carrier gas. A temperature program ramped from an initial 35 C to 240° C. at 60° C./min with a final hold for six minutes. The column was an Agilent Innowax 180 um ID×20 M long×0.18 um film thickness. Methyl but-2-enoate eluted at 1.601 minutes, methyl pent-2-enoate eluted at 1.846 minutes, methyl 3-hydroxybutanoate eluted at 2.631 minutes and methyl-3-hydroxypentanoate eluted at 2.846 minutes. The peaks were identified by searching the mass spectrum of the peak apex against the NIST 2007 mass spectral library. Quantitation of these four components was accomplished by comparing peak areas of reaction samples to a standard containing known concentrations of these four components.

Methyl 3-hydroxybutanoate, methyl but-2-enoate, methyl-3-hydroxypentanoate, and methyl pent-2-enoate were observed to be produced in each of the reactions above.

methyl 3-hydroxybutanoate: m/z=118
methyl but-2-enoate: m/z=100
methyl-3-hydroxypentanoate: m/z=132
methyl pent-2-enoate: m/z=114

Further, the ratio of the alkyl hydroxyalkanoates and alkyl alkenoates varied depending on the reaction temperature and pressure, and reaction time, and the ratios for the three reactions performed are summarized in Table 2 below.

TABLE 2

| Reaction # | Ratio of methyl 3-hydroxybutanoate to but-2-enoate | Ratio of methyl-3-hydroxypentanoate to methyl pent-2-enoate |
|---|---|---|
| 1 | 2.16 | 1.75 |
| 2 | 7.08 | 4.83 |
| 3 | 8.1 | 5.6 |

What is claimed is:

1. A method, comprising contacting a polyhydroxyalkanoate with a nucleophile to convert at least a portion of the polyhydroxyalkanoate to a polyhydroxyalkanoate derivative, the polyhydroxyalkanoate having a structure of Formula A:

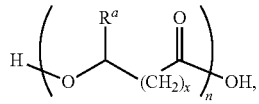

(A)

wherein $R^a$ is an aliphatic group; x is an integer greater than or equal to 1; and n is an integer greater than or equal to 20;

the nucleophile having a Formula of $R^b$—W—H, wherein W is O, NH, or S; and the polyhydroxyalkanoate derivative having a Formula of

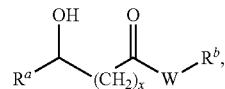

wherein $R^b$ is alkyl;
wherein:
(i) the nucleophile is a critical nucleophile, a supercritical nucleophile or a near-critical nucleophile; or
(ii) the method further comprises heating the polyhydroxyalkanoate and the nucleophile to critical, supercritical or near-critical conditions to produce the polyhydroxyalkanoate derivative; or
both (i) and (ii).

2. The method of claim 1, wherein W is O.
3. The method of claim 1, wherein W is NH.
4. The method of claim 1, wherein W is S.
5. The method of claim 1, wherein $R^b$ is $C_1$-$C_{20}$ alkyl, $C_1$-$C_{10}$ alkyl, or $C_1$-$C_6$ alkyl.
6. The method of claim 5, wherein $R^b$ is methyl or ethyl.
7. The method of claim 1, wherein the polyhydroxyalkanoate is contacted with the nucleophile at a temperature between 150° C. and 350° C.; and at a pressure between 500 psi and 3000 psi.
8. The method of claim 1, wherein the polyhydroxyalkanoate and the nucleophile are further contacted with a solvent, a base, or both a solvent and a base, to convert at least a portion of the polyhydroxyalkanoate to the polyhydroxyalkanoate derivative.
9. The method of claim 8, wherein the solvent comprises an organic solvent.
10. The method of claim 8, wherein the solvent comprises chloroform, dichloromethane, dichloroethane, methyl acetate, ethyl acetate, propyl acetate, butyl acetate, acetonitrile, acetone, acetic acid, dioxane, diglyme, dioxin, tetrahydrofuran, pentane, hexane, heptane, benzene, toluene, xylene, trimethylbenzene, ethylbenzene, methylethylbenzene, or hexofluoroisopropanol, or a mixture thereof.
11. The method of claim 8, wherein the base is selected from the group consisting of an organic base, a carbonate salt, an oxide salt, a hydroxide salt, and a buffer, or a combination thereof.
12. A composition comprising methyl 3-hydroxybutanoate, methyl but-2-enoate, methyl-3-hydroxypentanoate, methyl pent-2-enoate, and a critical, supercritical or near-critical alcohol.

* * * * *